United States Patent [19]

Khaw et al.

[11] Patent Number: 5,223,242
[45] Date of Patent: Jun. 29, 1993

[54] NEGATIVELY CHARGED SPECIFIC AFFINITY REAGENTS

[75] Inventors: Ban A. Khaw, Milton, Mass.; Vladimir Torchilin; Alexander L. Klibanov, both of Moscow, U.S.S.R.

[73] Assignees: The General Hospital Corporation, Boston, Mass.; USSR Cardiology Research Centre, Moscow, U.S.S.R.

[21] Appl. No.: 840,638

[22] Filed: Feb. 21, 1992

Related U.S. Application Data

[63] Continuation of Ser. No. 298,370, Jan. 18, 1989, abandoned, and a continuation of Ser. No. 795,092, Nov. 5, 1985, abandoned.

[51] Int. Cl.$^5$ .................................................. A61K 43/00
[52] U.S. Cl. ........................................ 424/1.1; 424/2; 424/9; 424/486; 424/400
[58] Field of Search ................... 424/1.1, 2, 9, 400, 424/486

[56] References Cited

U.S. PATENT DOCUMENTS 4,046,722  9/1977  Rowland .................................. 424/9
4,731,239  3/1988  Gordon .................................... 424/9

FOREIGN PATENT DOCUMENTS 0000667  2/1979  European Pat. Off. ............... 424/9
0131361  1/1985  European Pat. Off. ............... 424/9
2299872  2/1976  France ................................... 424/9
2362119  4/1976  France ................................... 424/9
8402643  7/1984  World Int. Prop. O. .
8601112  2/1986  World Int. Prop. O. ............. 424/9

*Primary Examiner*—James H. Reamer
*Attorney, Agent, or Firm*—Fish & Richardson

[57] ABSTRACT

An in vivo imaging or therapeutic method including administering to a mammal a specific affinity reagent including a physiologically compatible polymer bonded to one or more specific affinity molecules capable of selectively binding to a predetermined substance or class of cells, and one or more reporter groups capable of providing detectable contrast between the predetermined substance or class of cells and cells or substances of the mammal to which the specific affinity reagent does not bind, or of killing cells of the predetermined class.

28 Claims, No Drawings

NEGATIVELY CHARGED SPECIFIC AFFINITY REAGENTS

This is a continuation of application Ser. No. 07/298,370, filed Jan. 18, 1989, now abandoned which is a continuation of of copending application Ser. No. 795,092 filed on Nov. 5, 1985, now abandoned.

BACKGROUND OF THE INVENTION

This invention relates to specific affinity reagents.

Specific affinity reagents (reagents in which a substance having specific affinity for a class of cells is coupled to a reporter group) are described in many patents and publications. (As used herein, "specific affinity" refers to the ability of a substance to bind to one substance or class of cells and to substantially fail to bind to other substances or classes of cells; "reporter group" refers to a substance which is delivered to the specific substance or cells by the specific affinity portion of the reagent, for a diagnostic or therapeutic purpose; examples are radioisotopes, paramagnetic contrast agents, and anti-cancer agents.) For example, Schall U.S. Pat. No. 4,152,411 and Hirschfeld U.S. Pat. No. 4,166,105 describe in vitro specific affinity immunoassay reagents in which polylysine is attached to an antibody and to multiple labels, e.g., fluorophores. Schall also generally mentions "spin labeled compounds [and] radiolabeled compounds".

SUMMARY OF THE INVENTION

In general, the invention features an in vivo imaging or therapeutic method including administering to a mammal a specific affinity reagent including a physiologically compatible polymer bonded to one or more specific affinity molecules capable of selectively binding to a predetermined substance or class of cells, and one or more reporter groups capable of providing detectable contrast between the predetermined substance or class of cells and cells or substances of the mammal to which the specific affinity reagent does not bind, or of killing cells of said predetermined class.

The specific affinity reagent used in the above method can be one composed of a physiologically compatible polymer containing a plurality of negatively charged groups, bonded to a specific affinity compound having specific affinity for a target substance or cells, and to at least one reporter group.

The polymeric portion of the specific affinity reagents of the invention permits the attachment of a plurality of reporter groups, permitting signal enhancement where the reporter group is one, e.g., a paramagnetic ion, which benefits from such enhancement. In addition, the negative charges on the polymer provide attachment sites for reporter groups, and also advantageously enhance the rate of blood clearance of the reagent, as will be explained in more detail below.

Other features and advantages of the invention will be apparent from the following description of the preferred embodiments thereof, and from the claims.

DESCRIPTION OF THE PREFERRED EMBODIMENTS

Preferred embodiments of the invention are described below.

STRUCTURE AND PROPERTIES OF SPECIFIC AFFINITY REAGENTS

The preferred specific affinity reagents of the invention are physiologically compatible, negatively-charged (under physiological conditions) reagents in which a polymeric backbone molecule, e.g., polylysine, is chemically attached to both a specific affinity molecule, e.g., an antibody, and to one or, more preferably, multiple, reporter groups. The reporter groups are preferably attached at primary or secondary amino sites on the polymer. When the reporter group is a paramagnetic substance, it is attached to the polymeric backbone via a chelating agent. When the reporter group is a substance other than a paragmagnetic substance, e.g., a radioactive substance, or cytotoxic substance, it is attached either via a chelating agent or via a chemical linking agent, e.g., iodobenzene.

The negative charge of the reagent is provided by, e.g., negatively-charged carboxylate groups which are part of the original polymeric backbone, e.g., the carboxy-terminal end of a polypeptide, or which are chemically attached to the polymeric backbone at primary or secondary amino sites not attached to reporter groups. Carboxylate groups can also serve as the sites for attachment of the specific affinity molecule (e.g., antibody) to the polymeric backbone. Preferably, each polymeric backbone molecule has at least 80, and more preferably at least 120, negative charges.

The negatively charged carboxylate groups thus serve two functions: First, they facilitate attachment of the specific affinity portion of the reagent during synthesis of the reagent by irreversibly blocking any free amino groups of the polymer which might otherwise react with carboxylate groups which are already attached to the polymer molecule (causing undesirable cyclization), or which are attached to other polymer molecules (causing undesirable crosslinking between polymer molecules). Second, when the reagents are administered to a patient for in vivo imaging, the negative charge which the carboxylate groups provide enhances the rate at which the kidneys clear the reagent from the patient's blood. The quality (particularly contrast) of the image in part depends on the degree to which the reporter group is bound to the target tissue (to which the specific affinity portion of the reagent is directed) compared to other tissues, and this rapid clearing minimizes the background signal from reporter groups present in the blood surrounding the target tissue.

The rate of blood clearance is also affected by the molecular weight of the specific affinity reagent; in general, the rate of clearance increases as the molecular weight decreases. Preferably, therefore, the molecular weight of the reagents of the invention is below 1,000–150,000 daltons, more preferably less than 75 kd.

Other general characteristics of components of the specific affinity reagents of the invention follow.

Polymeric Backbone

Suitable polymers for the polymeric backbone are physiologically compatible, non-crosslinked polymers containing primary and/or secondary amino sites. In order to achieve rapid blood clearance, the molecular weight of the polymer is preferably less than 100 kilodaltons (kd), and more preferably less than 50 kd. Examples of suitable polymers include polyethylene imine, the polyaminoacids, e.g., polylysine, polyarginine, polyhistidine, polyaspartic acid, polyglutamic acid, and heteropolymers of the foregoing, with polylysine being most preferred. Suitable polymers are available commercially, and can be made using conventional methods.

Specific Affinity Portion

The specific affinity portion of the reagent is an organic substituent which has affinity for (i.e., binds to a substantially greater degree to) the target substance or cells than for non-target substances or cells. Examples are antibodies specific for certain tissues, e.g., cardiac tissue, and hormones which are specific for hormone receptor-bearing cells, e.g., the peptide hormones such as thyrotropin releasing hormone. The antigen or cell type for which the specific affinity molecule is specific is relatively more plentiful or more accessible in the target tissue, compared to other tissues.

When the specific affinity portion is an antibody, it is most preferably only the Fab portion of an IgG polyclonal or monoclonal antibody; use of the entire antibody, including the Fc portion, which does not contribute to specificity, only undesirably adds to the molecular weight of the reagent, Prolonging blood clearance time and/or contributing to non-specific liver activity.

Suitable specific affinity molecules include antibodies against antigens characteristic of particular organs, or antigens which are more available for antibody binding in a diseased or healthy state than in the opposite state (e.g., anti-cardiac myosin, which binds to myosin exposed in cardiac tissue which has been damaged by an infarct); antibodies against tumor antigens; antibodies against hormones, e.g., human chorionic growth hormone (hCG), which are diagnostic for certain types of tumors; antibodies against biological particles, e.g., white blood cells, red blood cells, and platelets; anti-carcinoembryonic antigen (CEA), which specifically binds to certain tumors; and anti-alpha feto protein, which specifically binds to liver tissue.

Generally, the reagents contain between one and three specific affinity molecules per polymer molecule, with one being generally most preferred, in order to minimize molecular weight.

Reporter Groups

The reporter groups of the reagents of the invention are any chemical groups which, when bound to a target cell or tissue, provide detectable contrast between the target and surrounding cells or tissues, or kill the target cells or tissues. Examples are paramagnetic substances (for in vivo diagnostic NMR imaging), radioactive substances (for diagnostic radioactive imaging), or cytotoxic substances (for destroying unwanted tissue, e.g., primary and metastatic tumor loci).

The paramagnetic substance can be any paramagnetic ion of the transition metal or lanthanide series which has at least one, and preferably five or more, unpaired electrons, has a magnetic moment of at least 1.7 Bohr magneton, and has acceptably low toxicity at the dosage used. Suitable ions include gadolinium (III), iron (III), manganese (II and III), chromium (III), copper (II), dysprosium (III), terbium (III), holmium (III), erbium (III), and europium (III); the most preferred ion is gadolinium (III).

The radioactive substance can be any substance which emits gamma radiation (for detection by gamma scintigraphy), e.g., Tc-99m or In-111; or which emits positrons (for detection by positron emission tomography), e.g., Ga-67, Ga-68, Mn-52m, or Pb-203 The most preferred radioactive substance is In-111.

The cytotoxic substance can be any substance which is capable of killing biological tissue when administered to a patient. Suitable cytotoxic substances include ricin, diphtheria toxin, and alpha- and beta-emitters, e.g., Pb 212, with Pb 212 being the most preferred cytotoxic substance.

Generally, the number of reporter groups per polymer molecule depends on the class of reporter group used. In the case of paramagnetic ions such as gadolinium (III), it is desirable to attach as many reporter groups as possible to each polymer molecule, to maximize NMR contrast enhancement. Preferably, the number of paramagnetic reporter groups per polymer molecule is at least 50, and most preferably at least 100. Similarly, the number of cytotoxic molecules or atoms per polymer molecule is preferably maximized, to increase cytotoxicity, and thus the chances that any individual cell to which the polymeric reagent binds will be killed. The number of cytotoxic molecules or atoms per polymer molecule is preferably at least 2, more preferably at least 10.

In the case of radioactive substances used for in vivo imaging, e.g., In-III, the number of reporter groups per polymer molecule is preferably lower than in the case of paragmagnetic ions, because for radioactive substances, signal amplification generally is not needed; for radioactive substances, the primary advantage provided by the polymeric backbone is rather the clearance-promoting negative charge. Therefore, since expense, low molecular weight, and number of negatively charged sites are all more important than signal amplification in the case of radioactive substances, it is preferred that the number of such molecules or atoms per polymer molecule be between one and five, with one or two being most preferred.

Chelating Agent

The chelating agent is preferably negatively charged, and does not contain aryl groups, so that clearance of the specific affinity reagent is primarily via the kidneys rather than the liver. Examples of preferred chelating agents include diethylenetriaminepentaacetic acid (DTPA) and ethylenediaminetetraacetic acid (EDTA).

Preparation of Specific Affinity Reagents

In general, the preparation of the specific affinity reagents involves first covalently attaching the chelating agent, if one is needed for the attachment of the reporter group, at primary or secondary amino sites on the polymer. The number of chelating agent molecules attached depends on the number of reporter groups to be incorporated. If the reporter group is of a type which can be attached to the polymer without first derivatizing the polymer with a chelating agent, the first step is the attachment of the reporter group.

In the next step, any unreacted primary or secondary amino sites on the polymer are treated with a non-toxic organic diacid or acid anhydride to create carboxylate groups blocking any free amino sites. Suitable diacids and anhydrides include acetic anhydride succinic acid, succinic anhydride, maleic acid, and maleic anhydride; most preferred is succinic anhydride.

The next step involves covalently attaching the specific affinity portion to the polymer at a carboxylate site, e.g., using carbodiimide. If no chelating agent has been used, this step completes the process. If a chelating agent has been used, the reporter group is added next, and the resulting specific affinity reagents are either used immediately or lyophilized and stored for future use.

A description of the preparation of particular specific affinity reagents follows.

In-111-DTPA-Polylysine-Antimyosin Fab

DTPA was covalently attached to polylysine (4 kd average molecular weight), using the mixed anhydride method described in Krejcarek et al. (1977) Biochem. Biophys. Res. Comm. 77, 581. The DTPA-polylysine was then treated with excess succinic anhydride in 0.1N $NaHCO_3$ to block any unreacted primary or secondary amino groups with carboxylate groups. Following succinylation, the absence of amino groups was confirmed by trinitrobenzenesulfonic acid titration.

The succinylated DTPA-polylysine was then covalently attached to antimyosin IgG monoclonal antibody (Fab) using carbodiimide as follows. Fab fragments were prepared conventionally by digesting antimyosin IgG monoclonal antibody (produced and purified using conventional techniques, as generally described in Khaw et al. (1984) Hybridoma 3, 11) with mercuripapain. The succinylated DTPA-polylysine was dissolved in water (1-2 mg/ml) and the pH adjusted to 3.0-4.0 with 1N HCl. Carbodiimide was then added up to a concentration of 1-2 mg/ml, and the resulting solution was incubated for up to 10-15 minutes at room temperature. A solution of the Fab fragments in 0.05M borate buffer (1-2 mg/ml, pH 8.2) was added at the end of the incubation period, and the resulting solution was again incubated for one hour at room temperature. The solution was then applied to a Sephadex G-100 column (1.2×95 cm) and eluted to separate free and Fab-bound polymers; elution is monitored with a UV monitor. Under the reaction conditions described above, only minimal free polymer and free Fab fragments are detected, indicating that coupling of the polymer to the Fab fragments is approximately 100%.

The DTPA-polylysine-antimyosin Fab polymer was then labeled with In-111. In-111 $Cl_3$ (0.5-1.0 mCi) was added to an equal volume of 1M citrate buffer (pH 5.5), and the solution was then added to an aqueous solution of DTPA-polylysine-antimyosin Fab. The resulting solution was applied to a Sephadex G-25 column (10 ml) to separate chelated In-111 from free In-111 $Cl_3$. Total indium binding to the polymer can be determined by elemental analysis, or by tracer uptake.

In-111-DTPA-polylysine-antimyosin Fab, Mn-DTPA-polylysine-antimyosin Fab, Gd-DTPA-polylysine-antimyosin Fab, In-111-DTPA-polyethylene imine-antimyosin Fab, and Mn-DTPA-polyethylene imine-antimyosin Fab are prepared using methods analogous to the method described above. When the reporter group is Mn or Gd, total metal binding to the polymer is determined by NMR spectroscopy.

Use

The specific affinity reagents can be used as diagnostic agents (when the reporter groups are paramagnetic or radioactive substances) for a variety of medical disorders. The reagents enhance the NMR contrast between the target tissue to which the specific affinity portion is directed and other tissues, or radio-actively label the target tissues. In vivo imaging is then carried out using conventional methods, e.g., as described in Haber et al., U.S. Pat. No. 4036945 (imaging using antibody/radioisotope conjugates); and Khaw et al. U.S. pat. appln. Ser. No. 640,305 (NMR imaging using antibody/paramagnetic ion conjugates) assigned to the same assignee as the present application; both are hereby incorporated by refererence. The negative charge of the reagents minimizes the concentration of these substances in non-target tissues.

The reagents can also be used as therapeutic agents (when the reporter groups are cytotoxic substances) because the specific affinity portion is directed primarily to the unwanted cells, which are selectively killed while minimizing damage to healthy tissues.

The specific affinity reagents are preferably administered intravenously. Dosage will vary to some degree, depending on the reporter group. For example, when the reporter group is a paramagnetic substance, higher dosages may be required than when the reporter group is a radioactive or cytotoxic substance. In general, the dosage will be one which provides to the patient about 5-20 mg, more preferably about 10 mg, of the specific affinity compound.

In the case of paramagnetic or radioactive reporter groups, conventional NMR imaging or radioactive imaging (gamma scintigraphy or positron emission tomography), respectively, is carried out; the details of the procedure will be governed by the diagnostic information sought. Use of the specific affinity reagents can provide information regarding size, location, and characterization of primary and secondary tumor loci or of tissue damage sites, e.g., myocardial infarcts.

Ex vivo biodistribution studies carried out on excised mouse liver, kidneys, and blood performed 1 hour after the mice were injected with the specific affinity reagent In-111-DTPA-polylysine (14 kd)-antimyosin Fab demonstrated that this specific affinity reagent is primarily cleared by the kidneys.

Dogs with induced myocardial infarcts were injected intravenously with In-111-DTPA-polylysine (14 kd)-antimyosin Fab or In-111-DTPA-polylysine (4 kd)-antimyosin Fab, and subjected to gamma scintigraphy; the former reagent enabled visualization of the infarct within 1 hour after injection, while the latter reagent enabled visualization in about 15 minutes after injection.

Other embodiments are within the following claims.

We claim:

1. An in vivo imaging or therapeutic method comprising administering to a mammal a specific affinity reagent which is negatively charged under physiological conditions and has a molecular weight of 1-150 kd, said reagent being a physiologically compatible polymer containing primary or secondary amino sites (1) covalently bonded to one or more specific affinity molecules, which are selected from the group consisting of an antibody and a receptor-specific ligand, capable of selectively binding to a predetermined substance or class of cells, and (2) covalently bonded to multiple reporter groups, which are selected from the group consisting of a paramagnetic substance, a radioactive substance, and a cytotoxic substance, capable of providing detectable contrast between said predetermined substance or class of cells and other cells or substances of said mammal to which said specific affinity reagent does not bind, or capable of killing cells of said predetermined class.

2. The method of claim 1, wherein said specific affinity reagent has a molecular weight less than 75 kd.

3. The method of claim 1, wherein said polymer is non-crosslinked.

4. The method of claim 1, wherein said polymer is a polyethyleneimine.

5. The method of claim 1, wherein said polymer is a polyaminoacid.

6. The method of claim 5, wherein said polymer is selected from the group consisting of a polylysine, a polyarginine, a polyhistidine, a polyaspartic acid, a polyglutamic acid.

7. The method of claim 6, wherein said polymer is a polylysine.

8. The method of claim 1, wherein said specific affinity molecule is an antibody.

9. The method of claim 8, wherein said antibody is the a portion of an IgG antibody.

10. The method of claim 9, wherein said antibody is the Fab portion of an IgG antibody.

11. The method of claim 1, wherein the backbone of said polymer contains at least 80 negative charges.

12. The method of claim 1, wherein the backbone of said polymer contains at least 120 negative charges.

13. The method of claim 1, wherein said specific affinity reagent contains a plurality of negatively charged carboxylate groups.

14. The method of claim 1, wherein said reporter group is a paramagnetic metal ion attached to said polymer via a chelating agent.

15. A specific affinity reagent which is negatively charged under physiological conditions and physiologically compatible, said specific affinity reagent having a molecular weight of 1-150 kd comprising:
   a polymer containing primary or secondary amino sites,
   one or more specific affinity molecules selected from the group consisting of an antibody and a receptor-specific ligand, said specific affinity molecule being covalently bonded to said polymer and having specific affinity for a predetermined substance or cell, and
   multiple reporter groups selected from the group consisting of a paramagnetic substance, a radioactive substance, and a cytotoxic substance, said reporter groups being covalently bonded to said polymer and being capable of providing detectable contrast between said predetermined substance or class of cells and other cells or substances of said mammal to which said specific affinity reagent does not bind, or capable of killing cells of said predetermined class.

16. The method of claim 15, wherein said specific affinity reagent has a molecular weight less than 75 kd.

17. The method of claim 15, wherein said polymer is non-crosslinked.

18. The method of claim 15, wherein said polymer is a polyethyleneimine.

19. The method of claim 15, wherein said polymer is a polyaminoacid.

20. The method of claim 19, wherein said polymer is selected from the group consisting of a polylysine, a polyarginine, a polyhistidine, a polyaspartic acid, a polyglutamic acid.

21. The method of claim 20, wherein said polymer is a polylysine.

22. The method of claim 15, wherein said specific affinity molecule is an antibody.

23. The method of claim 22, wherein said antibody is a portion of an IgG antibody.

24. The method of claim 23, wherein said antibody is the Fab portion of an IgG antibody.

25. The method of claim 15, wherein the backbone of said polymer contains at least 80 negative charges.

26. The method of claim 15, wherein the backbone of said polymer contains at least 120 negative charges.

27. The method of claim 15, wherein said specific affinity reagent contains a plurality of negatively charged carboxylate groups.

28. The method of claim 15, wherein said reporter group is a paramagnetic metal ion attached to said polymer via a chelating agent.

* * * * *